United States Patent
Hsieh et al.

(10) Patent No.: US 8,703,462 B2
(45) Date of Patent: Apr. 22, 2014

(54) GENERATION OF RANDOM DOUBLE-STRAND BREAKS IN DNA USING ENZYMES

(75) Inventors: Pei-Chung Hsieh, Topsfield, MA (US); Chudi Guan, Wenham, MA (US)

(73) Assignee: New England Biolabs, Inc., Ipswich, MA (US)

( * ) Notice: Subject to any disclaimer, the term of this patent is extended or adjusted under 35 U.S.C. 154(b) by 332 days.

(21) Appl. No.: 13/140,901

(22) PCT Filed: Feb. 3, 2010

(86) PCT No.: PCT/US2010/023007
§ 371 (c)(1),
(2), (4) Date: Jun. 20, 2011

(87) PCT Pub. No.: WO2010/091060
PCT Pub. Date: Aug. 12, 2010

(65) Prior Publication Data
US 2011/0256593 A1    Oct. 20, 2011

Related U.S. Application Data

(60) Provisional application No. 61/149,675, filed on Feb. 3, 2009, provisional application No. 61/158,815, filed on Mar. 10, 2009, provisional application No. 61/275,531, filed on Aug. 31, 2009.

(51) Int. Cl.
| | | |
|---|---|---|
| C12N 9/16 | (2006.01) | |
| C12N 15/00 | (2006.01) | |
| C12Q 1/68 | (2006.01) | |
| C12Q 1/34 | (2006.01) | |
| C12P 19/30 | (2006.01) | |
| C07H 21/04 | (2006.01) | |
| C07H 21/02 | (2006.01) | |

(52) U.S. Cl.
USPC ............ 435/196; 435/440; 435/6.1; 435/18; 435/89; 536/23.1; 536/23.2

(58) Field of Classification Search
None
See application file for complete search history.

(56) References Cited

U.S. PATENT DOCUMENTS

| | | | | |
|---|---|---|---|---|
| 7,851,192 | B2 * | 12/2010 | Guan et al. | 435/196 |
| 8,048,664 | B2 * | 11/2011 | Guan et al. | 435/196 |
| 2007/0042379 | A1 * | 2/2007 | Guan et al. | 435/6 |

OTHER PUBLICATIONS

Wu et al. Cloning and Characterization of a Periplasmic Nuclease of *Vibrio vulnificus* and Its Role in Preventing Uptake of Foreign DNA. Appl. Environ. Microbiol. Jan. 2001 67:1 82-88; doi:10.1128/AEM.67.1.82-88.2001.*
Branden et al. Introduction to Protein Structure, Garland Publishing Inc., New York, p. 247, 1991.*
New England Biolabs: "Fragmentation of RT-PCR and PCR products with NEBNext™ dsDNA Fragmentase" Application Note Sep. 2009, XP002579031.
Anderson Nucleic Acids Res. 9 13 3015-27 1981.
Herrera and Chaires J. Mol. Biol. 236 2 405-11 1994.
Focareta and Manning Gene 53 1 31-40 1987.
Moulard et al Mol Microbiol 8 4 685-95 1993.
Jekel et al Gene 154 1 55-59 1995.
Chang et al Gene 122 1 175-80 1992.
Dodd et al FEMS Microbiol Lett 173 1 41-6 1999.
Wang et al Nucleic Acids Res. 35 584-94 2007.

* cited by examiner

*Primary Examiner* — Yong Pak
(74) *Attorney, Agent, or Firm* — New England Biolabs, Inc; Harriet M. Strimpel

(57) ABSTRACT

An enzyme preparation is described that includes a non-specific nuclease and a T7 Endo I mutant in a unit ratio of less than 1:200. This enzyme preparation may be used to generate double-stranded DNA fragments of a size suitable for DNA sequencing. The ends of the fragments can be readily modified as necessary to ligate adaptors or individual nucleotides to one strand of the double-stranded DNA fragments.

11 Claims, 10 Drawing Sheets

FIG. 5

```
       20    25    30    35    40    45    50    55
       AP    PSSFS AAKQQ AVKIY QDHPI SFYCG CDIEW QGKKG 60    65   *70    75    80    85    90
             IPNLE TCGYQ VRKSQ TRASR IEWEH VVPAW QFGHH 95    100   105   110   115   120   125
             RQCWQ KGGRK NCSKN DQQFR LMEAD LHNLT PAIGE 130   135   140   145   150   155   160
             VNGDR SNFNF SQWNG VDGVS YGRCE MQVNF KQRKV 165   170   175   180   185   190   195
             MPQTE LRGSI ARTYL YMSQE YGFQL SKQQQ QLMQA 200   205   210   215   220   225   230
             WNKSY PVDEW ECTRD DRIAK IQGNH NPFVQ QSCQT Q
```

(SEQ ID NO:5)

Figure 1: Fragmentation of HeLa cell gDNA analysed by agarose gel electrophoresis (A) and the BioAnalyzer 2100 (B). 5 µg of genomic HeLa DNA was incubated with NEBNext dsDNA Fragmentase for varying times as indicated. Fragmented DNA was purified using MinElute columns and analyzed by the BioAnalyzer 2100.

FIG. 8-3

Protocol:
Digestion with NEBNext dsDNA Fragmentase:
Careful preparation and concentration determination of the starting material are important for the success of this reaction.

The recommended range for starting material is 1-5 μg but lower or higher amounts can be used. The final DNA concentration in the reaction should be 0.05 μg/μl. Incubate reaction mix on ice for 5 minutes before adding NEBNext dsDNA Fragmentase. Add 2 μl of NEBNext dsDNA Fragmentase per μg DNA and incubate as described below.

1. Set up the digestion reaction using the following guidelines (note that NEBNext dsDNA Fragmentase should not be added at this point):

| Reaction Components | Starting DNA Amount (μg) | | | | |
|---|---|---|---|---|---|
| DNA (μg) | 1 | 2 | 3 | 4 | 5 |
| 10X Fragmentase Reaction Buffer (μl) | 2 | 4 | 6 | 8 | 10 |
| 100X BSA (μl) | 0.2 | 0.4 | 0.6 | 0.8 | 1.0 |
| dsDNA Fragmentase (μl) | 2 | 4 | 6 | 8 | 10 |
| Final Volume* (μl) | 20 | 40 | 60 | 80 | 100 |

2. Incubate on ice for 5 minutes

3. Add NEBNext dsDNA Fragmentase

4. Incubate at 37°C according to the recommended times below to generate the desired fragment size (see notes)

| Desired Fragment Size (bp) | Incubation Time (min) |
|---|---|
| 600-800 | 15 |
| 300-600 | 20 |
| 100-300 | 30 |

5. Add 5 μl of 0.5 M EDTA to stop the reaction

6. DNA fragments are ready for DNA end repair, size selection, or analysis.

End Repair: Clean up the fragmented DNA (e.g. column purification) then proceed with desired DNA end repair protocol. If DNA fragments are to be used for the Illumina® Genome Analyzer DNA sample preparation, add 1 μl of E. coli DNA Ligase for Fragmentase to the end repair reaction with ≥ 1 μg DNA or 0.5 μl of E. coli DNA Ligase for Fragmentase to the end repair reaction with < 1 μg DNA.

Agarose Gel Size Selection/Analysis: Samples can be loaded directly on to an agarose gel. It is not necessary to clean up the reactions prior to loading.

Polycarylamide Gel Analysis: Clean up the fragmented DNA (e.g. column purification) prior to loading the samples on a PAGE gel.

Long Term Storage: Clean up the fragmented DNA (e.g. column purification) prior to long term storage.

Notes: For gDNA containing > 60% GC content, a longer incubation time with dsDNA Fragmentase is required to obtain the desired fragment size. See application note at www.neb.com.
PCR products and cDNA require a different incubation time with dsDNA Fragmentase to obtain the desired fragment size. See application notes at www.neb.com.
The E. coli DNA Ligase for Fragmentase contains NAD and is provided only for use in DNA end repair reactions following NEBNext dsDNA Fragmentase incubation and DNA clean up. Do not add E. coli DNA Ligase to the NEBNext dsDNA Fragmentase reaction.

References:
1. Patent pending
2. Unpublished observations

FOR RESEARCH PURPOSES ONLY.
Commercial use may require license from New England Biolabs, Inc., 240 County Road, Ipswich, MA. For information on commercial licensing, contact busdev@neb.com.

SEQUENCE LISTING

```
<160> NUMBER OF SEQ ID NOS: 5

<210> SEQ ID NO 1
<211> LENGTH: 36
<212> TYPE: DNA
<213> ORGANISM: artificial
<220> FEATURE:
<223> OTHER INFORMATION: primer

<400> SEQUENCE: 1
aaggttgaat tcgcgccacc tagctccttc tctgcc                              36

<210> SEQ ID NO 2
<211> LENGTH: 36
<212> TYPE: DNA
<213> ORGANISM: artificial
<220> FEATURE:
<223> OTHER INFORMATION: primer

<400> SEQUENCE: 2
ggtagaggat ccttattgag tttgacagga ttgctg                              36

<210> SEQ ID NO 3
<211> LENGTH: 30
<212> TYPE: DNA
<213> ORGANISM: artificial
<220> FEATURE:
<223> OTHER INFORMATION: primer

<400> SEQUENCE: 3
caagtacgca aaagccaaac tcgcgcatcg                                     30

<210> SEQ ID NO 4
<211> LENGTH: 30
```

-continued

```
<212> TYPE: DNA
<213> ORGANISM: artificial
<220> FEATURE:
<223> OTHER INFORMATION: primer

<400> SEQUENCE: 4
tgcgcgagtt tggcttttgc gtacttggta                                           30

<210> SEQ ID NO 5
<211> LENGTH: 213
<212> TYPE: PRT
<213> ORGANISM: Vibrio vulnificus
<220> FEATURE:
<221> NAME/KEY: MISC_FEATURE
<222> LOCATION: (69)..(69)
<223> OTHER INFORMATION: mutation where Q is mutated to S

<400> SEQUENCE: 5

Ala Pro Pro Ser Ser Phe Ser Ala Ala Lys Gln Gln Ala Val Lys Ile
1               5                   10                  15

Tyr Gln Asp His Pro Ile Ser Phe Tyr Cys Gly Cys Asp Ile Glu Trp
            20                  25                  30

Gln Gly Lys Lys Gly Ile Pro Asn Leu Glu Thr Cys Gly Tyr Gln Val
        35                  40                  45

Arg Lys Ser Gln Thr Arg Ala Ser Arg Ile Glu Trp Glu His Val Val
    50                  55                  60

Pro Ala Trp Gln Phe Gly His His Arg Gln Cys Trp Gln Lys Gly Gly
65                  70                  75                  80

Arg Lys Asn Cys Ser Lys Asn Asp Gln Gln Phe Arg Leu Met Glu Ala
                85                  90                  95

Asp Leu His Asn Leu Thr Pro Ala Ile Gly Glu Val Asn Gly Asp Arg
            100                 105                 110

Ser Asn Phe Asn Phe Ser Gln Trp Asn Gly Val Asp Gly Val Ser Tyr
        115                 120                 125

Gly Arg Cys Glu Met Gln Val Asn Phe Lys Gln Arg Lys Val Met Pro
    130                 135                 140

Gln Thr Glu Leu Arg Gly Ser Ile Ala Arg Thr Tyr Leu Tyr Met Ser
145                 150                 155                 160

Gln Glu Tyr Gly Phe Gln Leu Ser Lys Gln Gln Gln Gln Leu Met Gln
                165                 170                 175

Ala Trp Asn Lys Ser Tyr Pro Val Asp Glu Trp Glu Cys Thr Arg Asp
            180                 185                 190

Asp Arg Ile Ala Lys Ile Gln Gly Asn His Asn Pro Phe Val Gln Gln
        195                 200                 205

Ser Cys Gln Thr Gln
    210
```

GENERATION OF RANDOM DOUBLE-STRAND BREAKS IN DNA USING ENZYMES

CROSS REFERENCE

This application is a §371 application of international application number PCT/US2010/023007 filed on Feb. 3, 2010, which claims priority from U.S. provisional application No. 61/149,675 filed Feb. 3, 2009, 61/158,815 filed Mar. 9, 2009 and 61/275,531 filed Aug. 31, 2009, herein incorporated by reference.

BACKGROUND

Breaking genomic DNA into smaller distinct sizes of fragments is an important step in many sequencing technologies. Current mechanical fragmentation methods, such as sonication, adaptive-focused acoustics or nebulization, generate DNA fragments without base cleavage preferences. These methods, however, have the potential to damage DNA in places other than the phosphodiester bond, and have a lower efficiency of DNA recovery compared to enzymatic methods. On the other hand, enzymatic methods such as those that rely on restriction enzymes with specific recognition sequences produce fragments of a fixed specific size that may be large or small depending on the frequency of the occurrence of the recognition sequences. Thus far, studies on non-specific nucleases have shown that while there are no specific sequences required for recognition and cleavage, these enzymes show a preference for certain bases at the cleavage site (Anderson *Nucleic Acids Res.* 9(13): 3015-27 (1981); Herrera and Chaires *J. Mol. Biol.* 236(2): 405-11 (1994)).

SUMMARY

In an embodiment of the invention, a preparation is provided that includes a non-specific nuclease and a T7 Endo I mutant in a unit ratio of less than 1:200. In one example, the non-specific nuclease is *Vibrio vulnificus* (Vvn) nuclease, which has a mutation at Q69.

In another embodiment of the invention, a method is provided for generating fragments from large DNA suitable for sequencing that includes mixing a DNA of interest with a preparation, which contains a non-specific nuclease and a T7 Endo I mutant in a unit ratio of less than 1:200. The large DNA is cleaved into fragments of a size suitable for sequencing. Just as described above, an example of the non-specific nuclease for use in the method is Vvn nuclease more particularly a Vvn nuclease mutant with increased specific activity such as a mutation at Q69. Fragments of the large DNA may contain one or two blunt ends and can be further modified to ligate to adapters of the type used in sequencing DNA.

BRIEF DESCRIPTION OF THE DRAWINGS

FIG. 1A shows fragmentation of genomic DNA from Hela (cervix adenocarcinoma) cells, *E. coli* and CpG Hela cells (NEB#4007).

FIG. 1B shows fragmentation of genomic DNA from Herring sperm, lambda phage and Jurkat (human acute T-cell leukemia) cells.

FIG. 3A: Lane M is an NEB (Ipswich, Mass.) PCR marker (#N3234); lanes 1-9 are a 2-fold dilution series of enzyme beginning with 2 µg of MBP-Vvn nuclease (WT) in lane 1 (dilution buffer: 20 mM Tris-HCl (pH7.5), 50 mM NaCl, 0.15% Triton X-100 and 0.1 µg/ml BSA). The amount of enzyme used in lane 3 is defined as one gel unit in which 90% of the DNA fragments are less than 150 bp.

FIG. 3B: Lane M is a NEB (Ipswich, Mass.) PCR marker (#N3234); lanes 1-9 are a 2-fold dilution series of enzyme beginning with 1.5 µg of MBP-Vvn nuclease (mutant) in lane 1 (dilution buffer as above). The amount of enzyme used in lane 6 is defined as one gel unit.

Each lane represents a 50 µl reaction with 5 µg of different genomic DNAs (as indicated on the top of lanes) incubated with the same amount of 3 µl CB4v2 mix at 37° C. Each reaction was stopped with 15 mM EDTA after 30 min, 60 min and 90 min time intervals. DNA fragments were ethanol-precipitated and then air-dried. DNA pellets were resuspended in 50 µl of 1× gel loading dye, orange (NEB#B7022, Ipswich, Mass.) and loaded on a 2% agarose gel. Boxes indicate fragments around 150 bps.

FIG. 5 shows the amino acid sequence of Vvn nuclease (Q69S) mutant (SEQ ID NO:5). The amino acid sequence starts at position 19, since the signal peptide (1-18) is not cloned in the MBP-Vvn endonuclease (Q69S) construct. "*" indicates the position 69 where Q is mutated to S.

Figure 6:
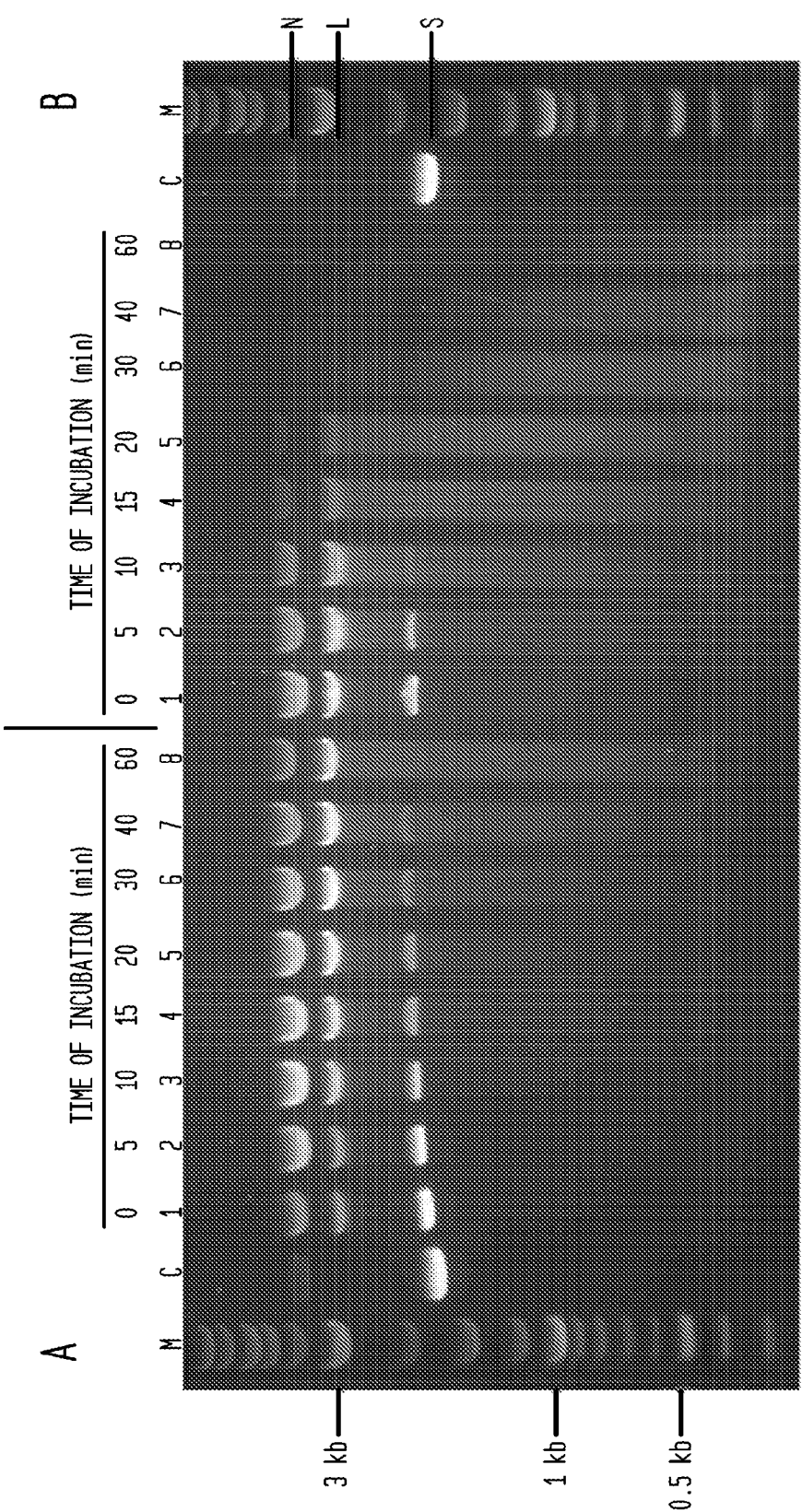

FIGS. 6A and 6B shows a comparison of the use of a plurality of different endonucleases in separate reaction vessels followed by the combination of fragmented products (FIG. 6A), and two endonucleases used together in the same reaction vessel (FIG. 6B) over a time range. M is the 2-Log DNA ladder and C is undigested pUC19. "-N-" indicates where nicked form of pUC19 migrates. "-L-" indicates where linear form of pUC19 migrates. "-S-" indicates where supercoiled form of pUC19 migrates.

FIG. 6A shows random double-stand cleavage using nicking enzyme MBP-Vvn endonuclease (Q69S) and MBP-T7 Endo I mutant, respectively. 8 µg of pUC19 were incubated with 1.376 TCA units of MBP-Vvn endonuclease (Q69S) in a 480 µl reaction. In another new tube, 8 µg of pUC19 were incubated with 5.6 units MBP-T7 Endo I mutant in a 480 μl of reaction. Samples were incubated at 37° C. 30 μl were removed from each incubation mix at 0, 5, 10, 15, 20, 30, 40, and 60 min and the reactions were stopped with addition of EDTA (final concentration 15 mM). Samples with the same incubation time were pooled together and loaded on a 0.8% agarose gel from lanes 1 to 8 corresponding to the incubation time from 0 to 60 min.

FIG. 6B shows random double-stand cleavage using MBP-T7 Endo I mutant and MBP-Vvn endonuclease endonuclease (Q69S) together. 16 μg of pUC19 were incubated with 1.376 T.C.A. Units/μl of MBP-Vvn endonuclease (Q69S) and 5.6 Units/μl MBP-T7 Endo I mutant (CB4V2) in a 480 μl reaction. Samples were incubated at 37° C. 60 μl were removed from each incubation mix at 0, 5, 10, 15, 20, 30, 40, and 60 min and the reactions were stopped with addition of EDTA (final concentration 15 mM). Samples were loaded on a 0.8% agarose gel from lane 1 to 8 corresponding to the incubation time from 0 to 60 min. A synergistic effect of MBP-T7 Endo I mutant and a nicking enzyme MBP-Vvn endonuclease (Q69S) was found on the generation of random DNA fragments.

Figure 7:
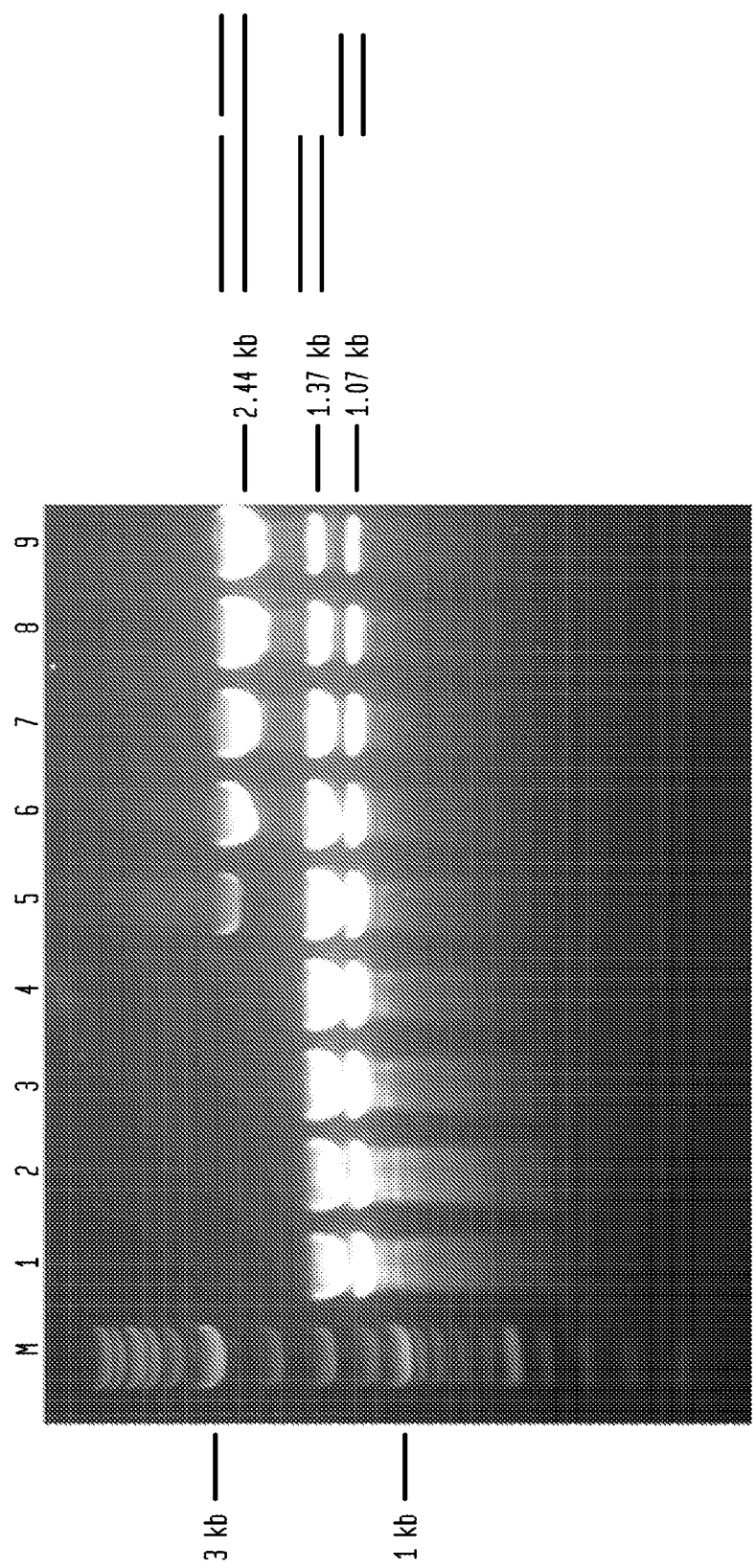

FIG. 7 shows a titration to determine a suitable unit ratio for a mixture of nucleases. Specific cleavage by T7 Endo I mutant against an existing nick site was determined by gel electrophoresis. The enzyme was two-fold serially diluted and a single unit was defined as the amount of enzyme capable of converting 90% of substrate into two fragments. The serial dilution was shown from most concentrated (lane 1) to most dilute (lane 9). Specific cleavage by T7 endonuclease mutant against the existed nicked site, which was created by BsaI/Nt.BstNBI during substrate preparation above, converted the linear-nicked 2.44 Kb double-stranded DNA (dsDNA) into two fragments (1.37 Kb and 1.07 Kb). Therefore, one unit of T7 endonuclease mutant was defined as the amount of enzyme required to convert 90% (as shown in lane 5) of 2 μg of the linear-nicked 2.44 kb dsDNA into two fragments (1.37 Kb and 1.07 Kb) at 37° C. for 1 hour with buffer containing 5 units of E. coli ligase, 60 μM NAD, 20 mM Tris-HCl (pH 7.5), 10 mM $MgCl_2$, 0.15% Triton X-100 and 50 mM NaCl in a 20 μl reaction. Lane "M" is the 2-log DNA ladder (NEB, Ipswich, Mass., #3200).

Figure 8:
Figure 1:
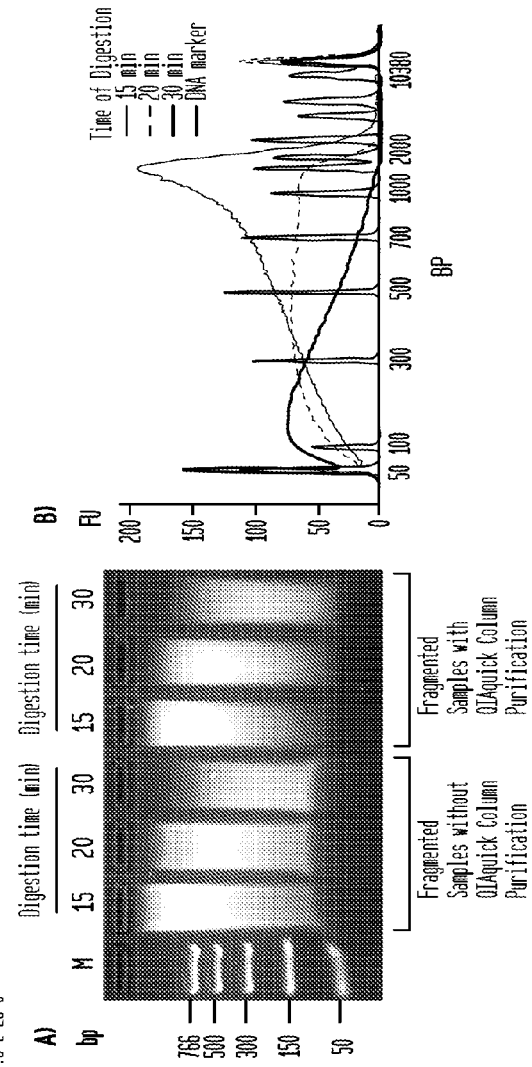
Figure 8:
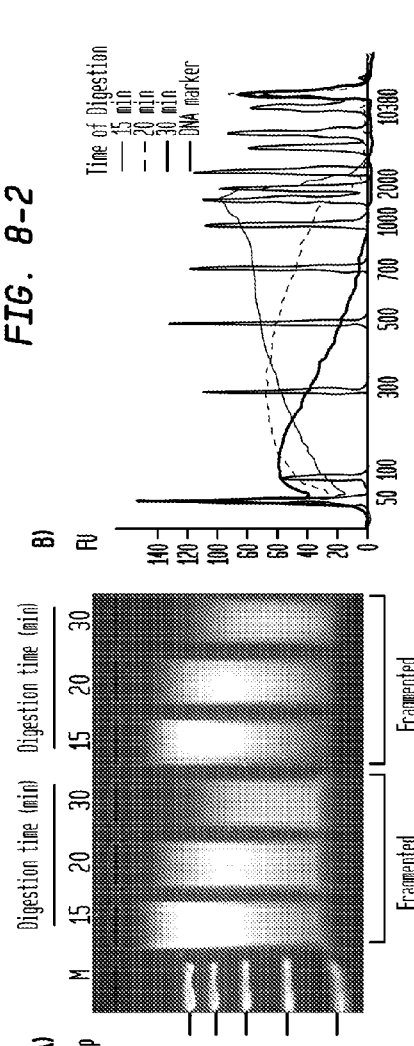
Figure 2:
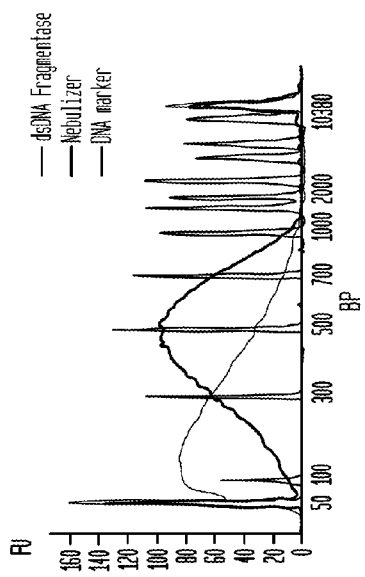

FIG. 8 shows a data card shipped with a product comprising an endonuclease mixture.

DETAILED DESCRIPTION OF THE EMBODIMENTS

In embodiments of the invention, compositions and methods are provided that rely on a mixture of enzymes in a preparation for producing double-stranded DNA fragments of approximately uniform size where the uniform size may be predetermined according to need and generated by, for example, varying the incubation time. The enzyme preparation reduces the number of non-productive nicks in dsDNA fragments compared with the dsDNA product of a non specific nuclease cleavage reaction alone by including a counter-nicking activity. The counter-nicking permits the creation of overhangs of defined length which will dissociate under normal dissociation conditions and which can be repaired to blunt ends for subsequent manipulation. Repair may involve chewing back a 3' overhang or synthesizing by means of a polymerase, a complementary sequence to a 5' overhang. Adaptors with blunt or single nucleotides overhang may then be ligated to the modified fragments. These fragments may then be used in various sequencing platforms.

Random fragmentation methods in the prior art generate overhangs but these are not discretely sized and create at least two problems. First, dissociation of the ends is not uniform as melting temperatures depend on the length and base composition of the overhang. Second, the presence of excess nicks, beyond those required for the dissociation of fragments, is a barrier to polymerization required in subsequent steps, including amplification and/or the actual sequencing reaction. Sequencing platforms involving physical continuity of the template would also be affected.

In an embodiment of the invention, the preparation contains a non-specific nuclease and a T7 endonuclease I or mutant thereof. Whereas a nuclease may be used which has a preference for cleaving AT or GC base pairs, preferably a nuclease is selected which does not have a significant bias for either GC or AT. An example of a nuclease belonging to this latter category is obtained from Vibrio vulnificus (Vvn) (GI: 2625684 Wu, et al. Appl Environ Microbiol 67(1): 82-8 (2001).

Other extracellular nucleases that may be utilized in the preparation include Dns from Vibrio cholera (Focareta and Manning Gene 53(1): 31-40 (1987); NucM from Erwinia chrysanthemi (Moulard, et al. Mol Microbiol 8(4): 685-95 (1993); Endo I from E. coli (Jekel, et al Gene 154(1): 55-59 (1995); Dns and DnsH from Aeromonas hydrophila (Chang et al. Gene 122(1): 175-80 (1992) and Dodd, et al. FEMS Microbiol Lett 173(1): 41-6 (1999); Wang, et al. Nucleic Acids Res 35: 584-94 (2007); and Wang, et al. Nucleic Acid Res. 35: 584-594 (2007)).

It is here demonstrated that mutations to the nuclease can result in improved specific activity. For example, mutations of Q69 of the Vvn endonuclease results in a nuclease with enhanced specific activity. In particular, the examples utilize Q69S. Mutant nucleases were found to be readily produced in host cells when, for example, the gene was coupled with the gene for MBP to create a fusion protein that accumulates in the periplasmic space for improved recovery of the mutant endonuclease.

The addition of a T7 Endo I mutant to an enzyme preparation containing a non-specific nuclease had an important beneficial effect on the generation of fragments with desired properties. Nicks created by non-specific nucleases that produce fragments of different sizes under denaturing conditions effectively disappeared in the presence of a T7 Endo I mutant because of its counter-nicking activity. The counter-nicking activity generated fragments with ends that could readily dissociate preferably 8 nucleotides or less from the nick site. Other beneficial effects of the enzyme mixture on dsDNA included production of DNA fragments which had a predictable overhang disposition and length that were suitable for repair or removal to permit attachment of adaptors that is sometimes required for DNA sequencing platforms.

In another embodiment of the invention a plurality of nucleases are combined in a reaction mixture where at least one nuclease is of the type capable of introducing random nicks throughout the DNA on either strand and a second nuclease is capable of counter-nicking in the immediate vicinity of this first nick, but in the opposite strand of the DNA duplex, thus causing a double-stranded DNA break.

This approach is demonstrated using, respectively, a non-specific nuclease derived from Vibrio and a mutant of T7 Endo I of the type described in U.S. Publication No. 2007-0042379, for example a T7 Endo I with a mutation in the bridge region. Enzyme fragments are predicted to be distributed along the genome.

Plasmid DNA and different types of genomic DNA (gDNA) were enzymatically cleaved into DNA fragments of a size suitable for sequencing methodologies using an enzyme preparation as described above. Following the fragmentation of the DNA, DNA fragments were gel-isolated and processed for next generation sequencing.

The assay provided in Example 2 may be used to identify the appropriate amount of nucleases for a selected time of incubation for any particular DNA or an appropriate time of incubation for a selected ratio of nucleases.

The unit ratio of the two nucleases (a nicking endonuclease such as a Vvn endonuclease mutant: counter-nicking nuclease such as a T7 Endo I mutant) is preferably less than 1:200 for example less than 1:100, for example, less than 1:10. The range may be 1:2 to 1:200.

One unit of T7 Endo I or mutant thereof was defined as the amount of enzyme required to convert 90% of 2 µg of the linear-nicked 2.44 kb dsDNA into two fragments (1.37 kb and 1.07 kb) at 37° C. for 1 hour.

One unit of Vvn nuclease and mutants thereof is defined as the amount of enzyme required to release 1 $A_{260}$ unit of acid soluble oligonucleotides in 30 min at 37° C.

In an embodiment of the invention, the optimal time of incubation for the DNA fragmentation reaction may be assayed according to whether the DNA falls in the range of greater than 60% GC (high GC content), 40%-60% GC (standard GC content), or less than 40% GC (low GC content). For example, the incubation time range may be typically in the range of 10 minutes to 120 minutes, for example, 15 minutes to 60 minutes.

All references cited herein, as well as U.S. Provisional Applications No. 61/149,675 filed Feb. 3, 2009, No. 61/158,815 filed Mar. 10, 2009 and No. 61/275,531 filed Aug. 31, 2009, are herein incorporated by reference.

EXAMPLES

"Large" constitutes a DNA having a size which requires fragmentation for sequencing.

T7 Endo I mutant refers to a T7 Endo I with a mutation in the bridge region between the two catalytic domains.

MBP-T7 Endo I mutant acts the same as T7 Endo I.

MBP-Vvn nuclease (WT or mutant) acts the same as Vvn nuclease (WT or mutant).

Non-specific nuclease refers to any DNA nuclease that does not recognize a specific DNA sequence. A DNA sequence consists of at least 2 nucleotides in a defined order. This excludes restriction endonucleases that recognize specific DNA sequences.

Example 1

Preparation of an Enzyme Mixture Containing Vvn or Mutant Thereof

The gene coding for periplasmic nuclease from Vvn was chemically synthesized. Vvn gene, absent its signal peptide, corresponds to amino acids 19 through 231 in FIG. 5 (SEQ ID NO:5). It was synthesized by PCR amplification using a pair of primers 1 (5'-AAGGTTGAATTCGCGCCACCTAGCTC-CTTCTCT GCC-3') (SEQ ID NO:1) and 2 (5'-GGTAGAG-GATCCTTATTGAGTTTGACAG GATTGCTG-3') (SEQ ID NO:2) and the fragment was cloned between the EcoRI and BamHI of pMALp4× vector (NEB, Ipswich, Mass., #N8104). The fusion protein MBP-Vvn endonuclease was expressed in the periplasmic compartment of E. coli and purified by an amylose affinity column to homogeneity. The MBP-Vvn nuclease (WT) was further purified by a Heparin column (GE Healthcare, Piscataway, N.J.). Protein concentration was determined by a Bradford assay (Bio-Rad Laboratories, Inc., Hercules, Calif.).

Figure 3:
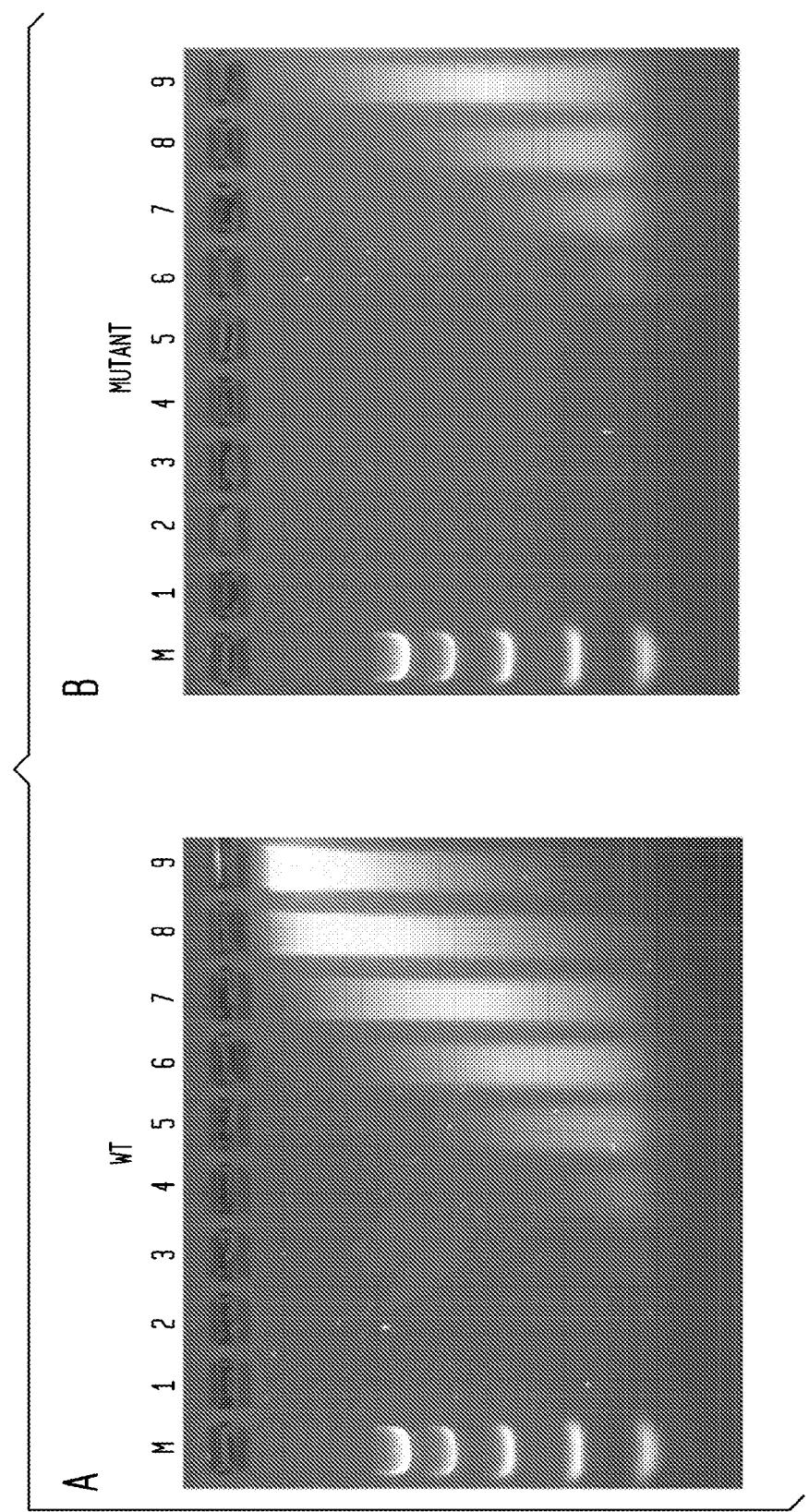
FIGS. 3A-3B show the generation of DNA fragments from 1 µg of Lambda DNA at 37° C. for 30 min in a 30 µl reaction using serial dilutions of nuclease: MBP-Vvn nuclease (wild-type (WT)) or MBP-Vvn nuclease (Q69S).
Figure 4:
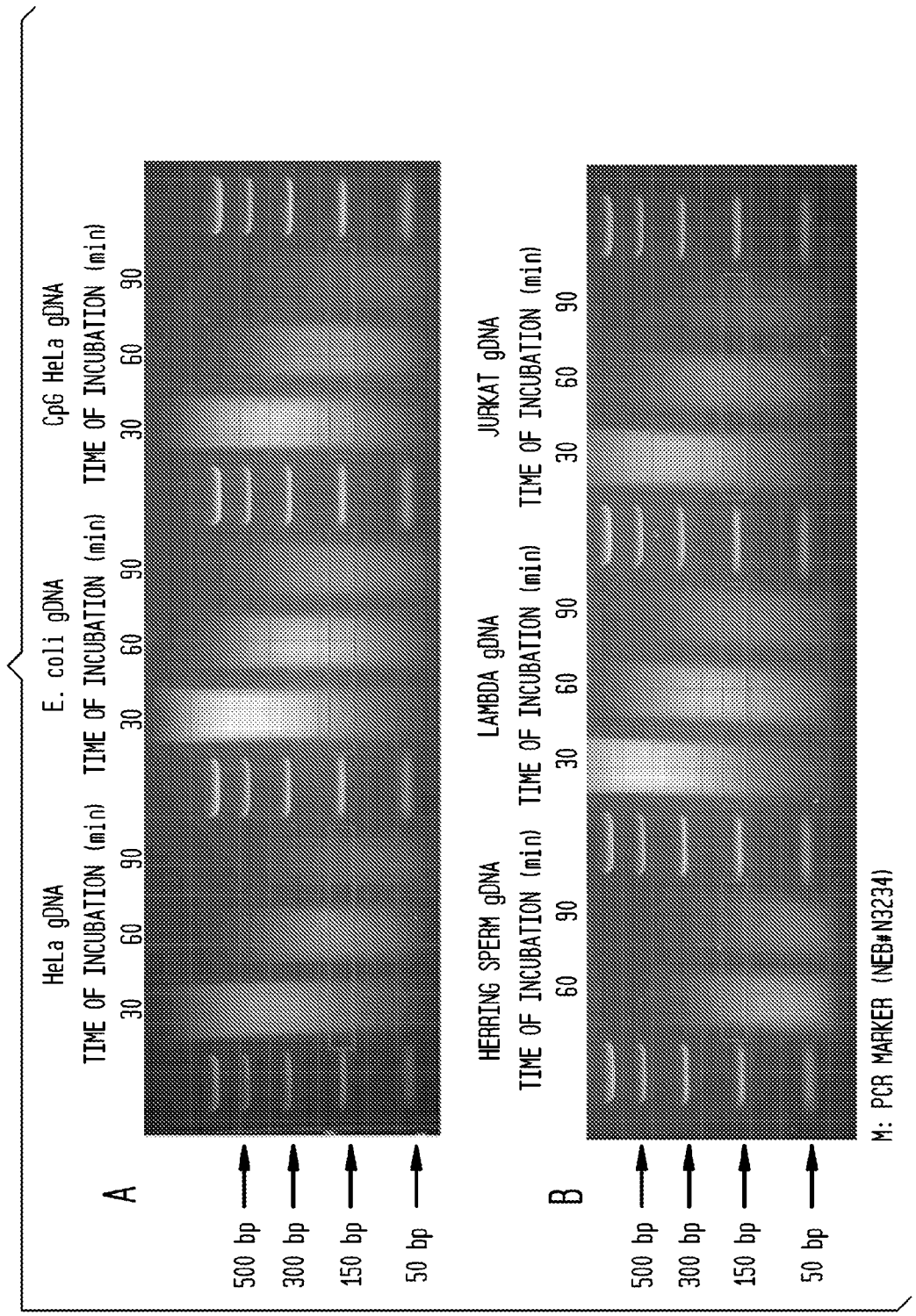
FIG. 4 shows the generation of DNA fragments using different incubation times for a mixture consisting of MBP-T7 EndoI mutant and MBP-Vvn nuclease (Q69S) (CB4v2). CB4v2 is a mixture of 2 volumes MBP-T7 EndoI mutant (0.16 units/µl) and 1 volume of MBP-Vvn nuclease (Q69S) (0.048 TCA units/µl).

A mutant MBP-Vvn endonuclease (Q69S) was created, which had 5-10 fold greater specific activity than MBP-Vvn endonuclease (WT) (FIGS. 3A-3B). To make the MBP-Vvn endonuclease (Q69S) mutant, primers 3 (5'-C AAGTACG-CAAAAGCCAAACTCGCGCAT CG-3') (SEQ ID NO:3) and 2 (SEQ ID NO:2) were used to amplify the C-terminal part of the Vvn gene, while primers 1 (SEQ ID NO:1) and 4 (5'-TGCGCGAGTTTGGCTTTTGCGTA CTTGGTA-3') (SEQ ID NO:4) were used to amplify the N-terminal region of the Vvn gene, excluding the signal peptide sequence. PCR fragments from each reaction were mixed and re-amplified from the intact Vvn gene using primers 1 (SEQ ID NO:1) and 2 (SEQ ID NO:2). The PCR product was cut with EcoRI and BamHI, then cloned into the pMAL-p4x vector cut with the same enzymes for the purpose of protein expression. The Vvn mutant endonuclease (Q69S) amino acid sequence is shown in FIG. 5. The fusion protein MBP-Vvn endonuclease (Q69S) was expressed in the periplasm of E. coil and purified by an amylose affinity column to homogeneity. Protein concentration was determined by Bradford assay (Bio-Rad Laboratories, Inc., Hercules, Calif.). When the Vvn mutant endonuclease was combined with T7 EndoI mutant (CB4v2), the mixture was found to efficiently fragment different sources and sizes of genomic DNA in a time-dependent manner (FIGS. 4A and 4B).

Example 2

Determining the Unit Ratio for Enzymes in the Mixture (a) Determining T7 Endo I Mutant Activity In order to prepare linear dsDNA with a specific nicked site, pNB1 was utilized (2.44 Kb). pNB1 is a plasmid with single sites for cleavage by Nt.BstNBI and BsaI. Cleavage with BsaI linearizes the plasmid, while Nt.BstNBI introduces a site-specific nick at its recognition site. The plasmid pNB1 was digested with Nt.BstNBI and BsaI restriction enzyme at 50° C. for one hour. Calf intestinal alkaline phosphatase was then added to the linear-nicked dsDNA and incubated at 37° C. for one hour. This treatment prevented sealing of the Nt.BstNBI nick by E. coli ligase during the subsequent assay. Fragmented dsDNA was separated from associated enzymes using Qiagen columns (Valencia, Calif.).

Treatment of the fragmented pNBI DNA with the T7 Endo I mutant introduced a counter-nick into the DNA strand approximately opposite the Nt.BstNBI nick to produce two fragments (1.37 kb and 1.07 kb) (see FIG. 7). One unit of T7 Endo I mutant was defined as the amount of enzyme required to convert 90% of 2 µg of the linear-nicked 2.44 kb dsDNA into two fragments (1.37 kb and 1.07 kb) at 37° C. for 1 hour with buffer containing 5 units of E. coli ligase, 60 µM NAD, 20 mM Tris-HCl (pH 7.5), 10 mM $MgCl_2$, 0.15% Triton X-100 and 50 mM NaCl. Lane 5 of FIG. 7 shows a reaction that satisfies this definition.

(b) Determining Mutant Vvn Endonuclease Activity

Sonicated calf thymus genomic DNA was used as substrates to assay the Vvn endonuclease activity. 5 µl of Vvn endonuclease mutant was added to 3 ml of a reaction mixture at 37° C. containing 20 mM Tris-HCl (pH 7.5), 10 mM $MgCl_2$, 0.15% Triton X-100, 50 mM NaCl, sonicated calf thymus gDNA (3 mg) and BSA (0.1 mg/ml), and incubation continued at 37° C. 500 µl of reaction mixture was removed and the endonuclease activity was stopped with 500 µl of 5% TCA after 10, 20, 30, 40 and 50 minute time intervals. These TCA-quenched samples were incubated on ice for an hour and centrifuged at 14000 rpm for 15 minutes to pellet-intacted DNA. Supernatant from each tube was carefully removed and an absorbance of the supernatant at 260 nm was measured. One unit of Vvn endonuclease mutant is defined as the amount of enzyme required to release 1 $A_{260}$ unit of acid soluble oligonucleotides in 30 min at 37° C.

(c) Determining the Unit Ratio of Mutant Vvn Endonuclease and Mutant T7 Endo I in the Nuclease Mixture The desired amounts of Vvn nuclease and T7 Endo I mutant were combined in a storage buffer of 10 mM Tris-HCl (pH 7.5), 50 mM NaCl, 0.1 mM EDTA, 200 µg/ml BSA and 50% glycerol at various ratios. DNA fragmentation buffer contained 20 mM Tris-HCl (pH7.5), 50 mM NaCl, 10 mM $MgCl_2$, 0.15% Triton X-100 and 0.1 mg/ml BSA.

In order to determine a suitable ratio of the two endonucleases, one endonuclease was maintained in a constant amount while the other nuclease was varied in concentration under otherwise similar reaction conditions using a TCA assay.

In the mixture of nucleases illustrated here, the unit ratio was approximately 3:1 for MBP-T7 Endo I mutant: MBP-Vvn endonucleases (Q69S) mutant. When the unit ratio was decreased to 2:1, the rate of DNA degradation reduced 50% as determined by the TCA assay described above. However, when the ratio was increased to 8:1, the rate only increased 14%.

Example 3

Figure 1:
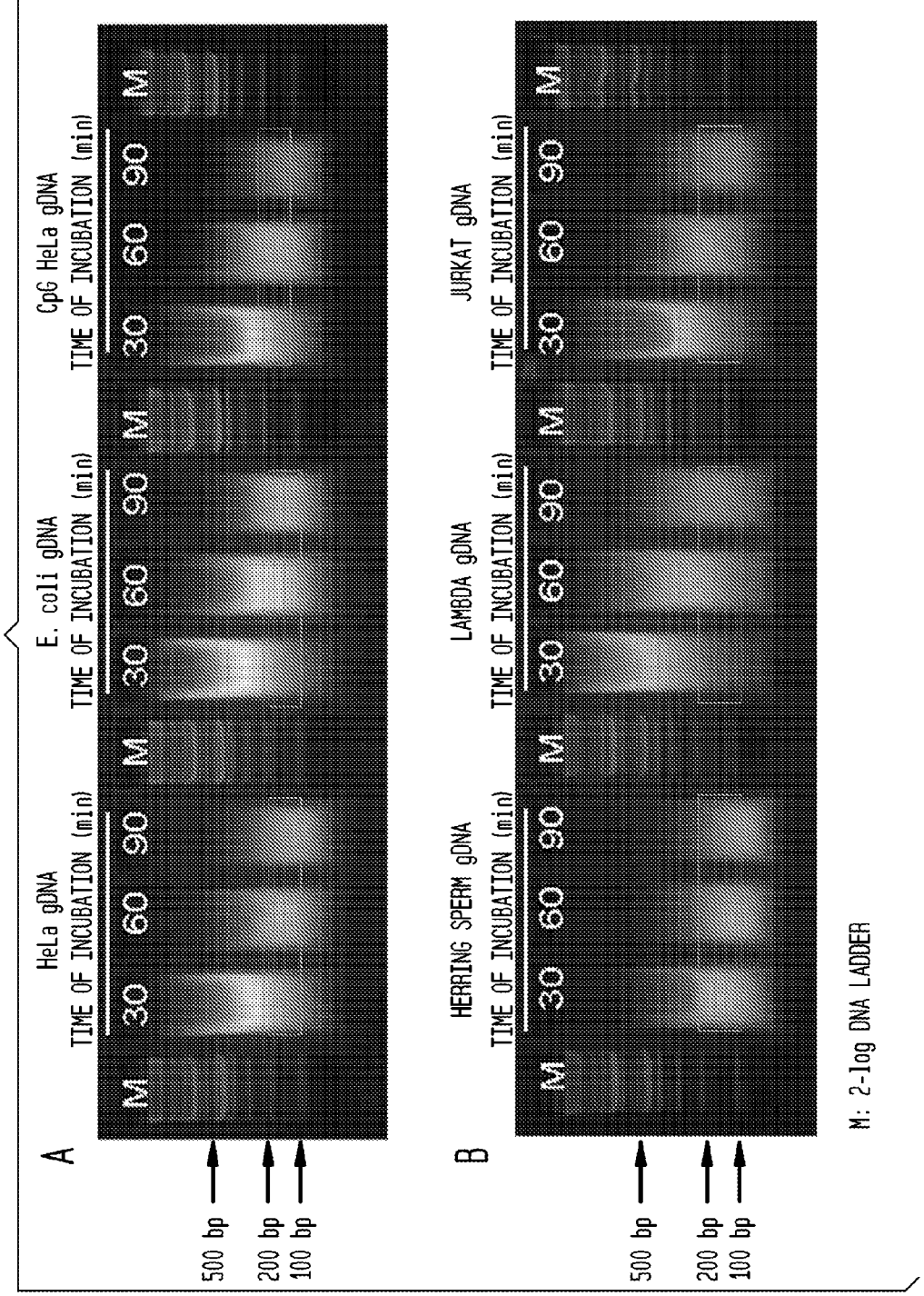
FIG. 1 shows DNA fragmentation using a combination of maltose-binding protein (MBP)-T7 Endo I mutant and MBP-Vvn. CB4 is a mixture of 2 volumes of MBP-T7 Endo I mutant (PA/A) (0.13 units/µl) and 1 volume of MBP-Vvn (0.14 units/µl)). Each lane represents a 30 µl reaction in which 5 µg of genomic DNA (as indicated on the top of lanes) was incubated with 3 µl of CB4 mix at 37° C. Each reaction was stopped with 15 mM EDTA after 30 min, 60 min and 90 min time intervals. DNA fragments were ethanol-precipitated and then air-dried. DNA pellets were resuspended in 50 µl of 1× gel loading dye, orange (New England Biolabs, Inc., (NEB), Ipswich, Mass., NEB#B7022) and loaded on a 2% agarose gel. Boxes indicate fragments around 100-200 bps.
Figure 2:
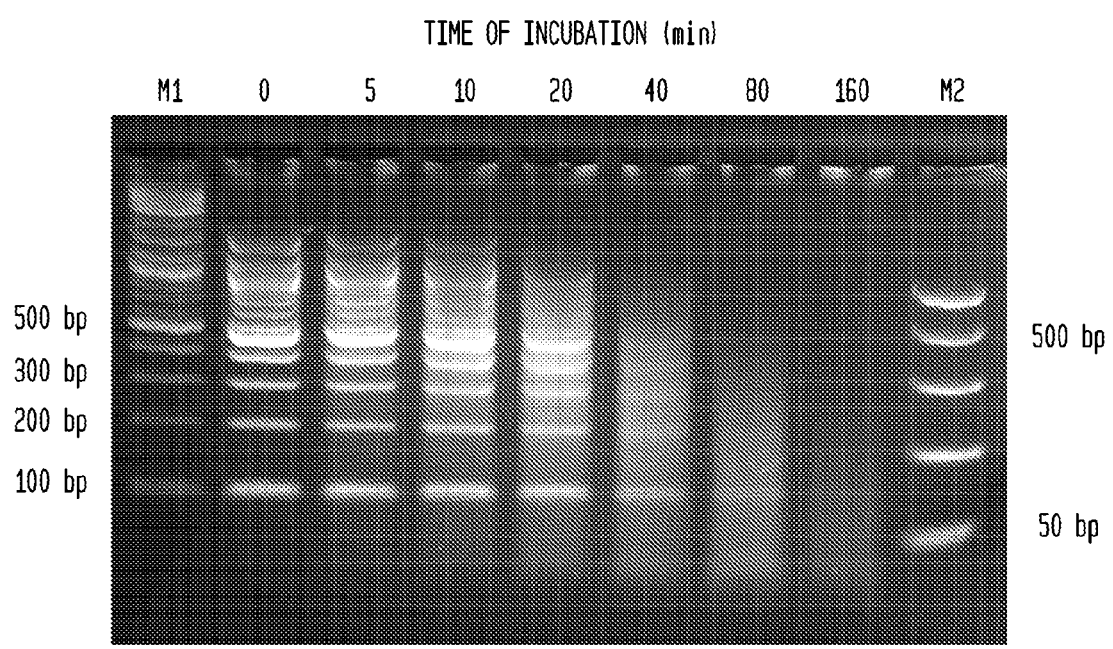
FIG. 2 shows the generation of DNA fragments as compared to two DNA ladders, M1, 2-Log DNA ladder (NEB #N3200, Ipswich, Mass.) and M2, NEB PCR marker (NEB #N3234, Ipswich, Mass.) using the CB4 mix. Seven reactions were set up and each 50 µl reaction containing 3 µl CB4 mix and 5 µg DNA ladder (NEB #N3231, Ipswich, Mass.) was incubated at 37° C. for various times and then terminated with 15 mM EDTA at 0, 5, 10, 20, 40, 80, 160 min time intervals. Fragments were loaded on 1% agarose gel.

Synergistic Effect of Combining a Nuclease with T7 Endo I Mutant in an Enzyme Mixture CB4 was shown to fragment genomic DNA from different sources and of different sizes in a time-dependent manner (FIG. 2). CB4 is a mixture of 2 volumes of MBP-T7 Endo I mutant (PA/A) (0.26 mg/ml) and 1 volume of MBP-Vvn (WT) (0.2 mg/ml)). CB4 also converted mixtures of small fragments with a size of 100-1500 bps into fragments of 100 to 150 bp (FIG. 2), a size suited to several current next generation sequencing platforms.

MBP-Vvn nuclease (Q69S) and MBP-T7 Endo I mutant in a mixture act synergistically to produce small double-stranded DNA fragments. FIGS. 6A and 6B show how treatment of plasmids with either MBP-Vvn nuclease (Q69S) or MBP-T7 Endo I PA/A over increasing times of incubation resulted in increased accumulation of nicked circular DNA, followed by formation of linear plasmid and degradation of this DNA into smaller fragments. However, when both enzymes were present in the same reaction mixture, conversion of the supercoiled plasmid into open circular or linearized DNA, and its degradation, was greatly increased (FIG. 6B) over that observed with the same concentrations of individual enzymes (FIG. 6A). For example, lane 6 in the combined samples (i.e., FIG. 6B) was devoid of discrete supercoiled, nicked, or linear plasmid, whereas abundant remnants of at least the nicked and linearized plasmid existed after incubation with the individual enzymes (FIG. 6A, lane 6).

The desired degradation of any particular DNA is a function of the size of the starting DNA, the size of the desired fragments and the time of incubation with a selected ratio of nucleases in the mixture.

---

What is claimed is:

1. A preparation, comprising:
a non-specific nicking nuclease and a T7 Endo I mutant in a unit ratio of less than 1:200, wherein the T7 Endo I mutant comprises a mutation in the bridge region between two catalytic domains.

2. The preparation according to claim 1, wherein the non-specific nicking nuclease is Vvn nuclease.

3. The preparation according to claim 2, wherein the Vvn nuclease has a mutation at Q69, which corresponds to amino acid position 51 of SEQ ID NO: 5.

4. A method for generating fragments suitable for sequencing from a large double-stranded DNA, comprising:

a. mixing the large DNA with a preparation according to claim 1; and b. cleaving the large DNA into fragments of a size suitable for sequencing.

5. A method according to claim 4, wherein non-specific nuclease is Vvn nuclease.

6. A method according to claim 4 or 5, wherein the Vvn nuclease has a mutation at Q69.

7. A method according to claim 6, further comprising: creating blunt ends on the fragments produced by cleavage in (b).

8. A method according to claim 7, further comprising: ligating adaptors with blunt ends or single nucleotide overhangs to one or both ends of the fragments.

9. A method according to any of claim 8, further comprising: ligating adaptors with blunt ends or single nucleotide overhangs to one or both ends of the fragments.

10. The preparation according to claim 3, wherein the mutation at Q69 is a Q69S mutation.

11. The preparation according to claim 1, wherein the preparation comprises a Vvn nuclease having a Q69S mutation that corresponds to amino acid position 51 of SEQ ID NO: 5 and a T7 Endo I mutant comprising a PA/A mutation in the bridge region.

\* \* \* \* \*